(12) United States Patent
Fischer

(10) Patent No.: US 9,918,819 B2
(45) Date of Patent: *Mar. 20, 2018

(54) IMPLANTABLE SLING SYSTEMS AND METHODS

(71) Applicant: Boston Scientific Scimed, Inc., Maple Grove, MN (US)

(72) Inventor: Brian G Fischer, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/161,271

(22) Filed: May 22, 2016

(65) Prior Publication Data

US 2016/0262862 A1    Sep. 15, 2016

Related U.S. Application Data

(63) Continuation of application No. 13/520,125, filed as application No. PCT/US2010/062546 on Dec. 30, 2010, now Pat. No. 9,345,473.

(Continued)

(51) Int. Cl.
*A61F 2/00* (2006.01)
*A61B 17/34* (2006.01)
(Continued)

(52) U.S. Cl.
CPC ...... *A61F 2/0045* (2013.01); *A61B 17/06109* (2013.01); *A61B 17/3468* (2013.01);
(Continued)

(58) Field of Classification Search
CPC ........ A61B 17/0401; A61B 2017/0409; A61B 17/0487; A61B 2017/06176;
(Continued)

(56) References Cited

U.S. PATENT DOCUMENTS

| 5,439,467 A | 8/1995 | Benderev et al. |
| 5,766,221 A | 6/1998 | Benderev et al. |

(Continued)

FOREIGN PATENT DOCUMENTS

| WO | 2005067802 A1 | 7/2005 |
| WO | 2007002012 A1 | 1/2007 |

(Continued)

OTHER PUBLICATIONS

Office Action for CA Application No. 2,785,830, dated Feb. 13, 2017, 5 pages.

(Continued)

*Primary Examiner* — Christine H Matthews
*Assistant Examiner* — Joshua D Lannu
(74) *Attorney, Agent, or Firm* — Brake Hughes Bellermann LLP

(57) ABSTRACT

Various embodiments of sling or implant systems are provided. The sling or implant systems can be employed to treat incontinence, prolapse, and like conditions. A needle delivery device can be included, wherein the delivery device includes a needle and a rotatable sheath. The rotatable sheath can rotate upon actuation relative to the needle to selectively deploy or disengage an implant anchor from the distal end of the needle.

21 Claims, 9 Drawing Sheets

Related U.S. Application Data

(60) Provisional application No. 61/291,210, filed on Dec. 30, 2009, provisional application No. 61/291,372, filed on Dec. 31, 2009, provisional application No. 61/291,363, filed on Dec. 31, 2009.

(51) Int. Cl.
*A61B 17/06* (2006.01)
*A61B 17/00* (2006.01)

(52) U.S. Cl.
CPC ...... *A61B 17/3496* (2013.01); *A61B 2017/00805* (2013.01); *A61B 2017/06042* (2013.01)

(58) Field of Classification Search
CPC ..... A61B 2017/045; A61B 2017/00805; A61F 2/0045; A61F 2220/0016
See application file for complete search history.

(56) References Cited

U.S. PATENT DOCUMENTS

| | | | |
|---|---|---|---|
| 2002/0161382 A1 | 10/2002 | Neisz et al. | |
| 2005/0143618 A1* | 6/2005 | Anderson | A61B 17/0401 600/29 |
| 2006/0173524 A1* | 8/2006 | Salahieh | A61F 2/2439 623/1.11 |
| 2006/0271074 A1* | 11/2006 | Ewers | A61B 17/0401 606/148 |
| 2007/0142846 A1 | 6/2007 | Catanese et al. | |
| 2008/0132753 A1* | 6/2008 | Goddard | A61B 17/06109 600/37 |
| 2011/0160529 A1* | 6/2011 | Crawford | A61F 2/0045 600/37 |

FOREIGN PATENT DOCUMENTS

| | | | | |
|---|---|---|---|---|
| WO | 2007123978 A2 | 11/2007 | | |
| WO | WO 2009038781 A1 * | 3/2009 | ....... | A61B 17/00234 |

OTHER PUBLICATIONS

Second Examination Report for AU Application No. 2015202455, dated Jan. 31, 2017, 6 pages.
Office Action for Canadian Application No. 2,785,830, dated Feb. 13, 2017, 5 pages.
Second Examination Report for Australian Application No. 2015202455, dated Jan. 31, 2017, 6 pages.

\* cited by examiner

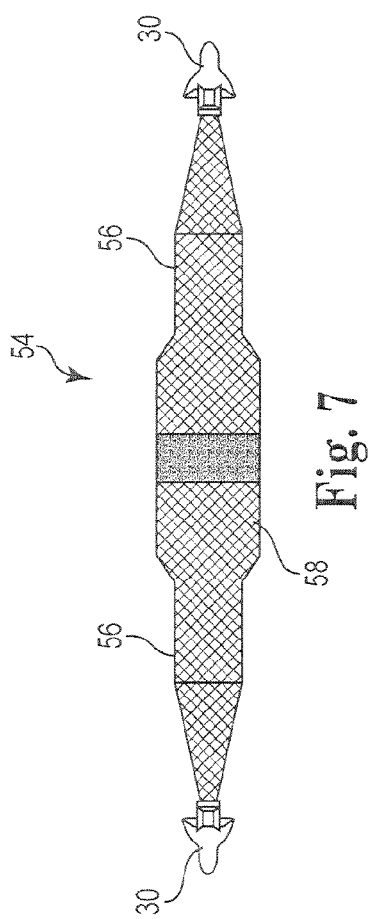
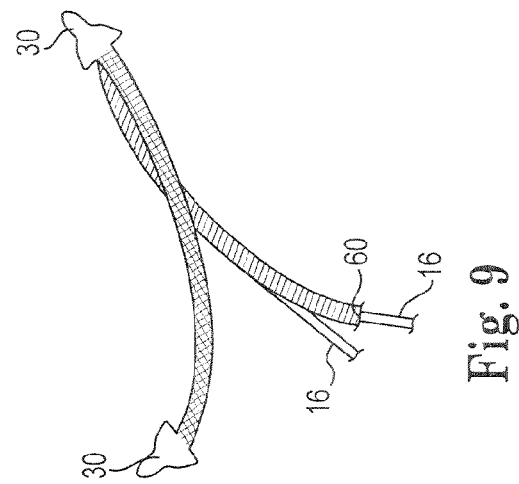
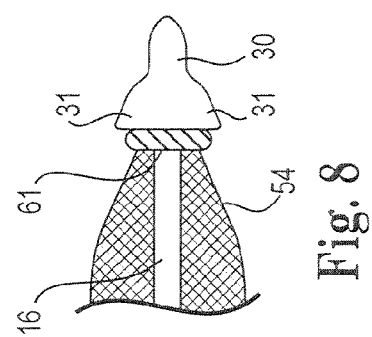

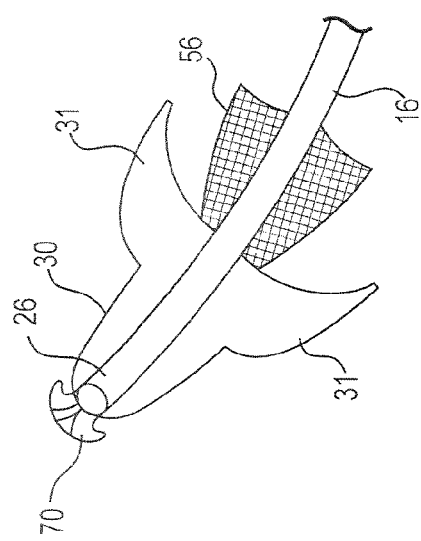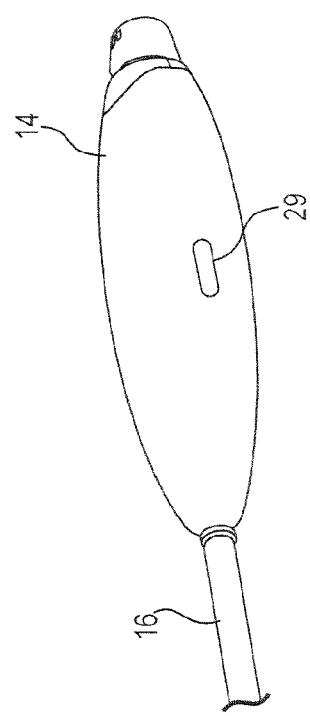
Fig. 19

IMPLANTABLE SLING SYSTEMS AND METHODS

PRIORITY

This Application is a Continuation Application of U.S. application Ser. No. 13/520,125, filed Sep. 13, 2012, which is a 371 of PCT Application No. PCT/US10/62546, filed Dec. 30, 2010, which claims priority to and the benefit of U.S. Provisional Application Nos. 61/291,210, filed Dec. 30, 2009, 61/291,372, filed Dec. 31, 2009, and 61/291,363, filed Dec. 31, 2009; wherein each of the referenced applications are fully incorporated herein by reference.

FIELD OF THE INVENTION

The present invention relates generally to surgical methods and apparatus and, more specifically, to surgically implantable mesh or sling devices and methods for using and deploying the same.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implantable mesh that can be used to treat incontinence, and/or pelvic organ prolapse and other conditions.

SUMMARY OF THE INVENTION

The present invention describes pelvic mesh implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness.

Embodiments of the systems can include one or more needle delivery devices and an implant. The implants can be elongate sling devices, or pelvic prolapse implants. Each implant can generally include a support portion, one or more extension or arm portions, and one or more end anchors. One or more portions of the slings or implants can be constructed of a mesh material.

Various embodiments of the systems can include a needle delivery device having an actuation mechanism and rotatable sheath. The rotatable sheath can shroud or otherwise be provided along at least a portion of the curved or straight needle of the delivery device, and in operable communication with the actuation mechanism. Engagement or activation of the actuation mechanism rotates the sheath to selectively disengage or deploy the anchors of the implant from a distal tip of the needle device.

Certain embodiments of the implant and delivery device can include tube, sheath or like docking or re-docking features to facilitate selective engagement and deployment of the anchor and implant from the device. The anchors can be adapted to penetrate and engage in selected target tissue within the pelvis proximate, at, adjacent, or lateral the urethra, vagina, obturator foramen, endopelvic fascia, bladder, pelvic floor, elevator muscles, and the like.

Embodiments of the present invention may be incorporated into or provided with various commercial products marketed by American Medical Systems of Minnetonka, Minn., e.g., the MiniArc® or MiniArc® Precise Sling Systems.

BRIEF DESCRIPTION OF THE DRAWINGS

FIG. 7 is a top view of a mesh sling implant in accordance with embodiments of the present invention.

FIGS. 8-9 are schematic views of a sling implant, and tube docking/re-docking features or portions in accordance with embodiments of the present invention.

FIG. 19 is shows a needle delivery device and distal needle tip configuration in accordance with embodiments of the present invention.

DETAILED DESCRIPTION OF PREFERRED EMBODIMENTS

The present invention generally provides a sling or implant system 10 adapted for insertion to selectively deploy one or more implants or slings to treat various pelvic conditions, including incontinence (e.g., fecal or urinary), pelvic organ prolapse (e.g., rectal or vaginal), or other like conditions. The systems 10 of the present invention can include delivery devices, implants, docking/re-docking features and like configurations, features and devices to facilitate deployment and sling implantation.

The various systems, features and methods detailed herein are envisioned for use with or can incorporate devices, portions or methods of known pelvic implants, tissue or organ repair systems (e.g., for male and female), including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2010/0105979 2010/0261955, 2002/151762 and 2002/147382. Accordingly, the above-identified disclosures are fully incorporated herein by reference in their entirety.

Figure 1:
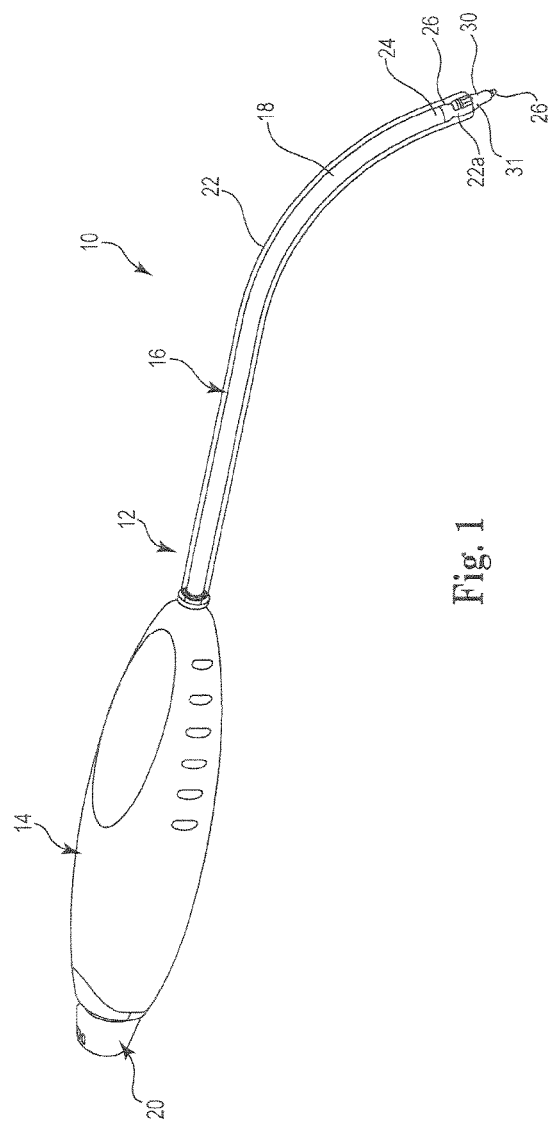
FIG. 1 is a perspective view of a needle delivery device with a rotatable sheath in accordance with embodiments of the present invention.
Figure 2:
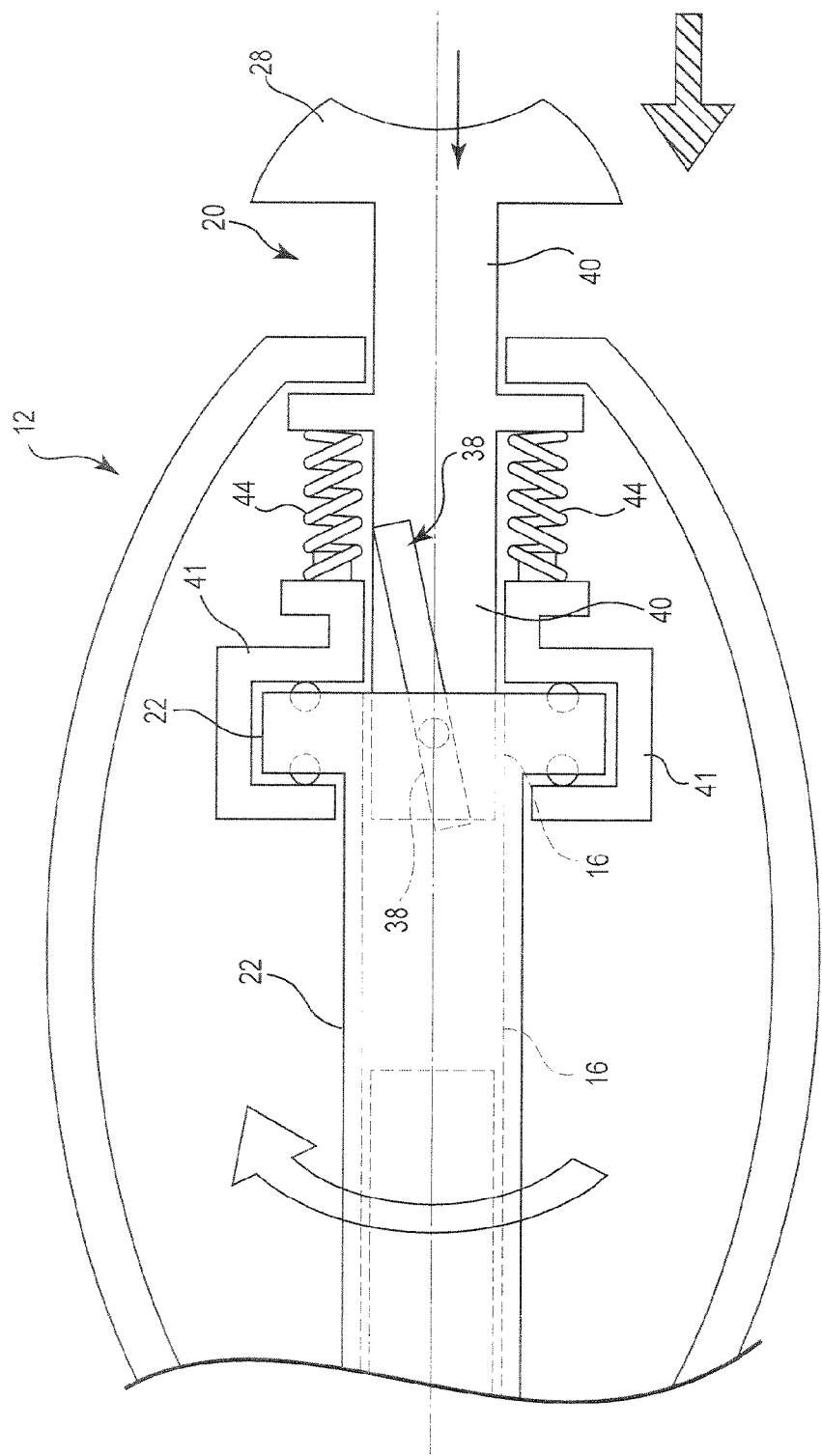
FIG. 2 is a schematic close-up cross-sectional view of a portion of a needle delivery device handle and actuation mechanism in accordance with embodiments of the present invention.
Figure 3:
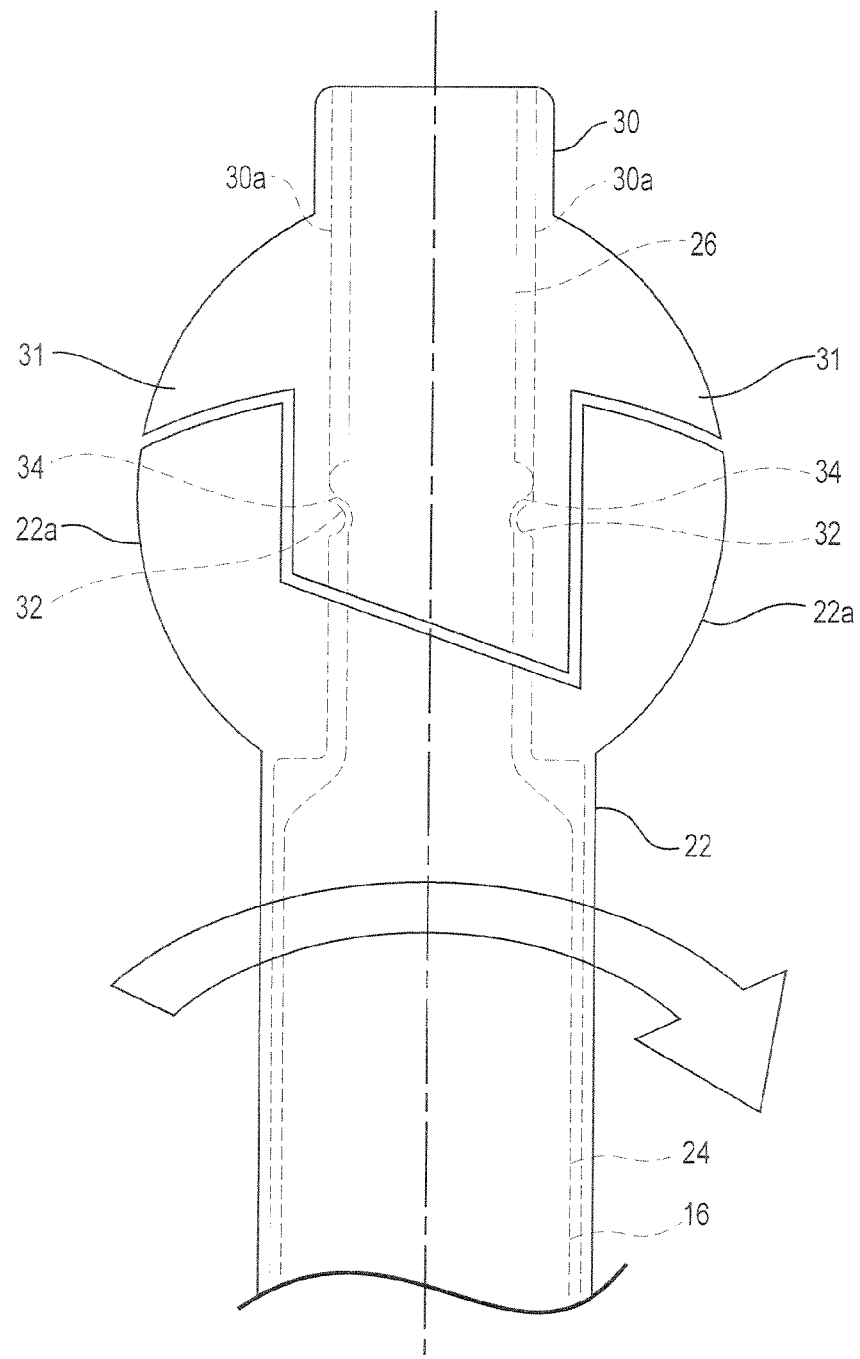
FIG. 3 is a schematic close-up cross-sectional view of a portion of a needle delivery device distal end, anchor and rotatable sheath in accordance with embodiments of the present invention.

Referring generally to FIGS. 1-3, embodiments of an implant delivery system 10 are shown. The implant delivery system 10 can include a delivery tool 12, having a handle 14 and a needle portion 16. The handle portion 14 can include an actuation mechanism 20. The needle portion 16 can include a needle 18, a rotatable sheath or tube 22 and a distal end portion 24. In various embodiments, the needle 18 can be hollow, solid, curved, straight, helical, or can take on a myriad of other like and compatible configurations. The sheath 22 generally shrouds a length of the needle portion 16. The distal end portion 24 can include an anchor retention and deployment tip 26.

The actuation mechanism 20 can include a button, slider or like actuator 28 in operable communication with at least the sheath 22 such that engagement or activation of the button 28 will cause the sheath 22 to rotate about the needle 16. FIGS. 2-3 show an embodiment of the handle 14 and distal end portion 24 of the needle 16, wherein pressing on or actuation of the button 28 rotates the sheath 22 to correspondingly deploy, push or release a tissue anchor 30 from the needle portion 16. For retention (e.g., snap engagement) of the anchor 30 on the distal tip 26 of the needle portion, embodiments of the anchor 30 can include small protrusions, ribs, ridges, indents or other features 32 within the lumen 30a of the anchor 30. Corresponding, reversed or mirrored features 34 can be included at the end of the engaged distal tip 26. Snap engagement of the anchor 30 to the tip 26 is provided with the features 32, 34 such that the anchor 30 is retained on the needle portion 16 until the time of selective disengagement during final deployment within the patient's soft tissue. This configuration further allows for audible and tactile feedback of engagement of the anchor 30 to the tip 26. The level of force needed to snap engage anchor 30 and needle 16 can vary greatly, depending on the materials used for the components, and the construct of the features 32, 34. As depicted in FIG. 3, the anchor 30 is initially keyed to the needle body (e.g., tip 26) such that the anchor 30 cannot rotate, but can slide longitudinally. The sheath 22 can include a barb guard 22a at the end proximate or at the distal end 24. The barb guard 22a and anchor 30 interface can be angled, straight, undulating, or take on various other configurations to facilitate the described snap engagement or retention. The anchor 30 can include one or more tines 31 adapted to mateably or abuttably engage corresponding surfaces or extensions in the barb guard 22a.

The actuation mechanism 20 within the handle 14 can include a cam or follower mechanism 38 causing the sheath 22 to rotate around the needle shaft, such that the anchor 30 is caused to move longitudinally in a distal direction off of the end of the tip 26. This longitudinal distal force on the anchor 30 by the cam mechanism 38 can be sufficient to overcome the retention force of the anchor 30 with the needle in accordance with the anchor retention features described herein. As such, once the retention features are disengaged, the anchor 30 slides freely from its distal position on the needle tip 26 and is thereby deployed.

Referring to FIG. 2, actuation mechanism 20 within the handle can include a barrel 40 adapted for longitudinal displacement within the handle 14 housing. In general, the barrel 40 is restricted from rotational movement. A proximal end of the sheath 22 is constrained within a housing boundary 41 such that it can rotate, but does not move longitudinally. As such, longitudinal movement of the button 28 and barrel 40 causes the sheath 22 to rotate. For example, the sheath 22 can include one or more cam mechanisms or features 38, generally opposed by 180 degrees. The barrel 40 can further include one or more cams, generally opposed by 180 degrees. Compression springs 44 are included and provide a resetting feature.

Various advantages of the embodiments depicted in FIGS. 1-3 include, a self-resetting handle mechanism 20, a convenient handle actuator 28, anchor tines 31 retained until deployment, minimization of tissue disruption by anchor tines 31 during anchor deployment, repeatable and secure engagement and disengagement of the anchor 30 and the needle 16, as well as tactile and audible feedback with the anchor 30 engagement. The various features and mechanisms, or portions thereof, can be constructed of known and compatible metals and polymers.

Figure 4:
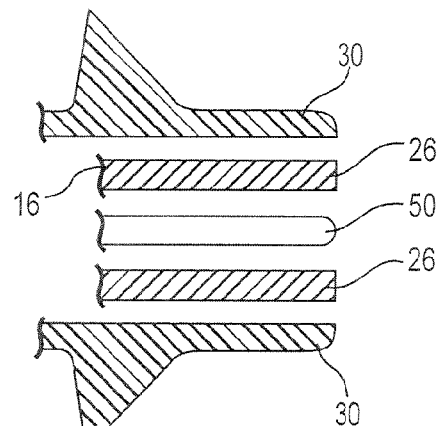
FIGS. 4-6 are schematic cross-sectional partial views of an anchor, distal needle tip, and retention feature in accordance with embodiments of the present invention.
Figure 5:
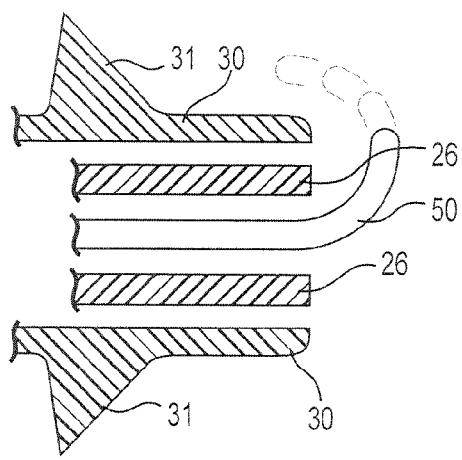
Figure 6:
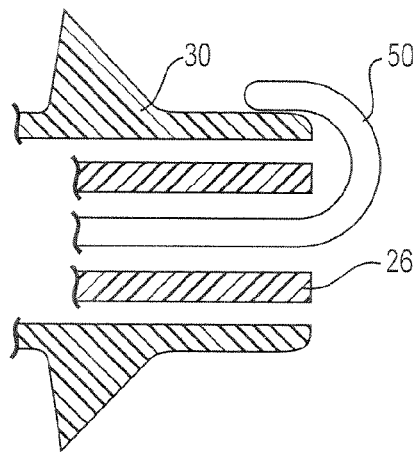

Referring generally to FIGS. 4-6, selective engagement and retention of the anchor 30 to the needle tip 26 for various embodiments are shown. Such embodiments can include a selectively extendable and retractable fixation member 50. The fixation member 50 is adapted to traverse, generally longitudinally, within or along the lumen of the hollow needle body 16. The fixation member 50 can be a shape memory wire or member, such as a Nitinol or other like wire materials, adapted to move in and out of the distal tip portion 26 of the needle 16 upon actuation by an end user (e.g., button or actuator in the handle 14). Various handle 14 and actuation members 28 can be included in operable communication with the member 50 to facilitate displacement of the member 50.

While traversing within the needle 16, or along an outer portion of the needle in alternative embodiments, the member 50 is retained in a generally longitudinal configuration or shape (FIG. 4). As a portion of the member 50 is deployed out of the distal tip 26 of the needle 16, at least a portion of the member 50 is generally free to resume its default shape, such as a curved or angled configuration. As such, the tip or end portion of the member 50 will tend to move or curve around the distal tip 26 to engage or otherwise retain the anchor 30 attached or provided at the distal tip 26 (FIG. 5). This will, in turn, secure the anchor 30 to the distal tip 26 such that the anchor 30 can be inserted, positioned and ultimately fixated within a target tissue site (FIG. 6).

Upon reaching the desired target tissue site, the anchor 30 can be released from the distal tip 26 of the needle 16. Namely, the user can retract or otherwise activate the member 50 such that the member 50 retreats or retracts back toward or into the needle tip 26. At this point, the needle 16 can be retracted, leaving the tissue anchor 30 in place or fixated to the target tissue site.

Referring generally to FIGS. 7-19, various embodiments of implantable sling or implant systems 54 are provided. In general, the implant 54 can be a mesh or patterned strut construct having extending portions 56 and a support portion 58. One or more anchors 30 can be included at the end portions of the extension portions 56. Various portions of the implants 54 can be constructed of polymer materials, such as a film or sheet material of polypropylene, polyethylene, fluoropolymers or like compatible materials.

Referring generally to FIGS. 8-19, various embodiments of the mesh or sling implant 54 are shown with various docking or re-docking features. Such re-docking features facilitate repositioning of the anchor 30 with the introducer needle 16, in or out of the patient's body. In one embodiment, a tube or sheath 60 is provided such that the introducer needle 16 is insertable within the tube 60. The tube 60 may encircle the needle 16, it may be integral with the sling or implant 54, or even made from the mesh or other portion of the implant 54. In other instances, the tube 60 can be a separate component, and may be semi-circular, v-shaped, or u-shaped rather than completely encircling the needle 16, to at least partially guide the needle 16 along the tube 60. The tube 60 can be removed with an axial tensile pull or with relative rotation (e.g., similar to a plastic bottle cap). As shown in FIG. 8, the tear away portion can include a thin tab 61 adapted to break the anchor 30 away from the needle 16 and/or tube 60 with a twisting motion.

The needle 16 can generally provide a counter force to the twist or rotation to ensure the anchor 30 position is not changed. Further, a barb guard can be included at a distal portion of the tube 60. The barb guard can provide a guard to prevent the tines 31 of the anchor 30 from engaging tissue until the moment of deployment, and can further serve to abut or provide a slight press fit with the anchor 30. The tube 60 provides a convenient, consistent and stable means of engagement or docking the needle 16 with the anchors 30 or sling 54.

The tube or sheath 60 can be torn away after positioning of the anchor 30 and deployment within target tissue. This can be done bilaterally for the two tubes 60, e.g., both extension portions 56 or end anchors 30. Perforations, slots, grooves, and like configurations can be included with the tube 60 to facilitate this tear away feature. The needle 16, or a portion thereof, can be inserted into an end of the hollow tube 60, or can be guided along an external surface or portion of the tube 60 (both shown in FIG. 9)

As detailed, the guide sheath or tube 60 can extend from the implant 54 to provide a channel or groove path for the needle to engage the anchors 30. The guide tube 60 can be constructed in a c-shaped, u-shaped, v-shaped or similar configuration to facilitate guidance of the needle. The tube 60 can be weakly attached (e.g., tear away bonds or welds) to the mesh implant 54 such that the tube 60 can be selectively torn away or otherwise removed from the implant.

Figure 10:
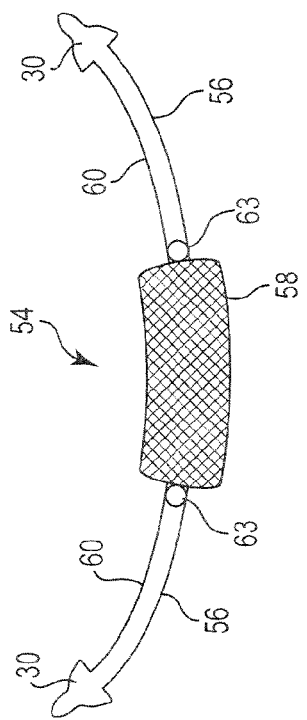
FIG. 10 is a top view of sling implant having a mesh support portion, and extension portions or arms in accordance with embodiments of the present invention.
Figure 13:
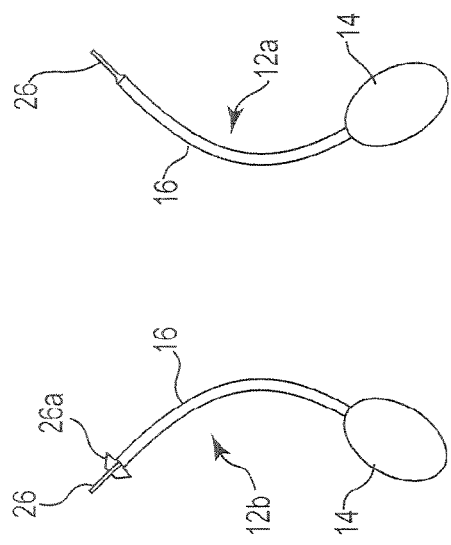
FIGS. 12-15 show a sling implant and delivery system having multiple needle delivery devices in accordance with embodiments of the present invention.
Figure 15:
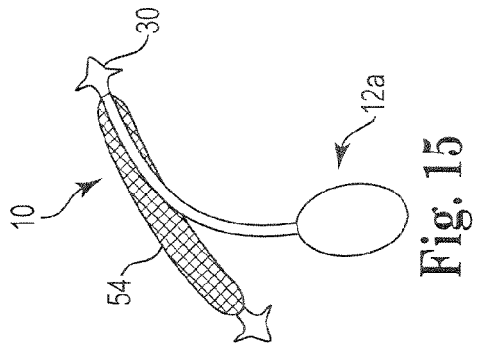
Figure 12:
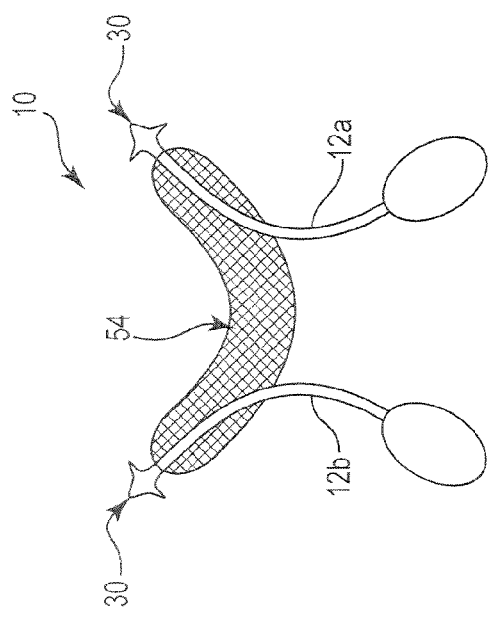
Figure 14:
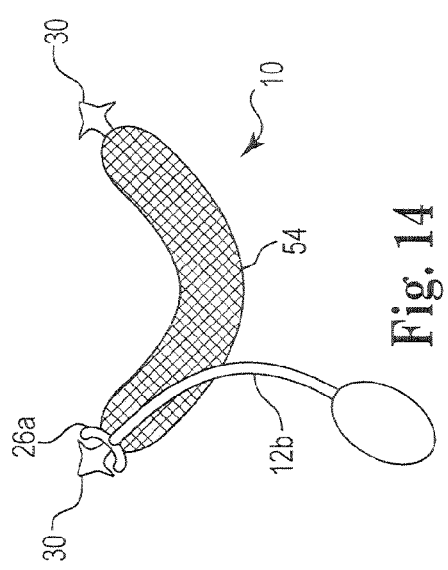

The embodiment of FIG. 10 can include an implant 54 having the center mesh support portion 58, with lateral arms or extension portions 56 extending therefrom. The lateral arms 56 can be included with the tube 60 to again facilitate engagement and guidance of a needle 16 to the anchors 30. The lateral arms 56 can be constructed of wrapped mesh, hollow tube material, or take on a myriad of other configurations and material constructs. The arms 56 can further include one or more ports 63 adapted to facilitate entry and exit of the needle 16 or tip 26 for engagement and deployment of the anchor 30.

Figure 11:
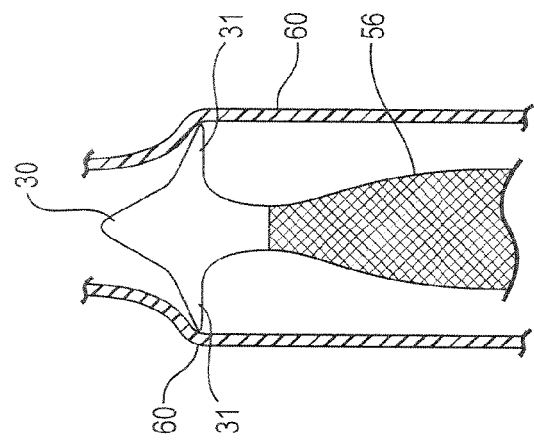
FIG. 11 is a close-up partial schematic view of a tube or sheath extending substantially around a sling implant and anchor in accordance with embodiments of the present invention.

As shown in FIG. 11, various sheath or tube 60 embodiments can extend above or around at least a portion of the anchors 30. As such, the tube 60 can be longitudinally moved to slide away from the anchors 30 at deployment or implantation. The tube 60 can be perforated or scored to further facilitate removal. Again, the tube 60 can protect the barbs or tines 31 of the anchor 30 from engaging tissue until final implantation.

Referring to FIGS. 12-15, the sling or implant system 10 can include two needle delivery devices 12 rather than a single needle device. The needle device 12 can be adapted to engage and manipulate a corresponding anchor 30 of the implant 54. As such, deployment, manipulation, and tensioning can be applied to the implant 54 by one or both of the needle devices. In one embodiment, as shown in FIGS. 11-15, one of the needle devices 12a can include a barb guard 26a, with the other device 12b not having a barb guard. The needle device 12a can be used to anchor the sling on a second target tissue location, thus facilitating tensioning (advancing and retracting needle/anchor) without engaging the barbs 31 of the anchor 30 with the tissue until the desired tension is obtained.

In various embodiments, the anchors 30 can include pivotable, moveable, expandable or collapsible tines 31. In an initial insertion stage, the tines 31 lay generally flat or substantially angled toward the implant 54 or anchor 30 body to prevent engagement of the tines 31 with tissue. Upon deployment, the tines 31 can be forcibly or automatically extended out to facilitate engagement with the target tissue location. Expansion and retraction of the tines 31 can be achieved by suture releases, or mechanical or manual means. The anchor 30 or tines 31 can be constructed of acceptable or known materials (e.g., shape memory) and constructs to facilitate such moveable or collapsible functionality.

Figure 16:
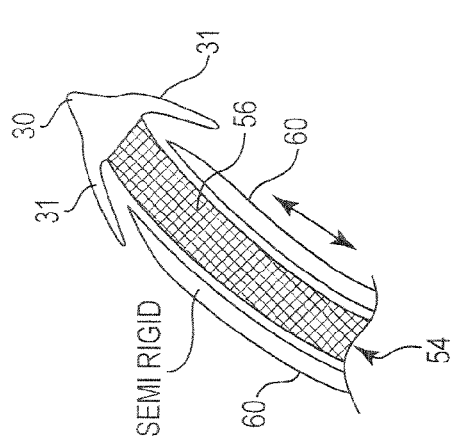
FIG. 16 is a close-up partial cross-sectional schematic view of a slidable tube or sheath, implant and anchor in accordance with embodiments of the present invention.
Figure 17:
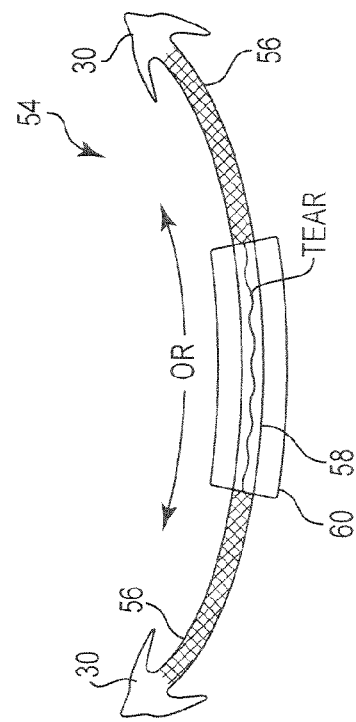
FIG. 17 shows a sling implant system having a slidable or displaceable tube or sheath in accordance with embodiments of the present invention.

Referring to FIGS. 16-17, the tube or sheath 60 can be free floating or adapted to split along a length thereof to facilitate guidance of the needle 16 and movability of the tube 60. The tube 60 can be constructed of flexible, rigid, or semi-rigid materials known by those of skill in the art. As such, the tube 60 can selectively engage and disengage with the tines 31 of the anchors 30. The movability of the tube 60 allows it to slide along a length of the sling 54 as shown in FIG. 17, thus facilitating easy removal and optimal positioning during deployment.

Figure 18:
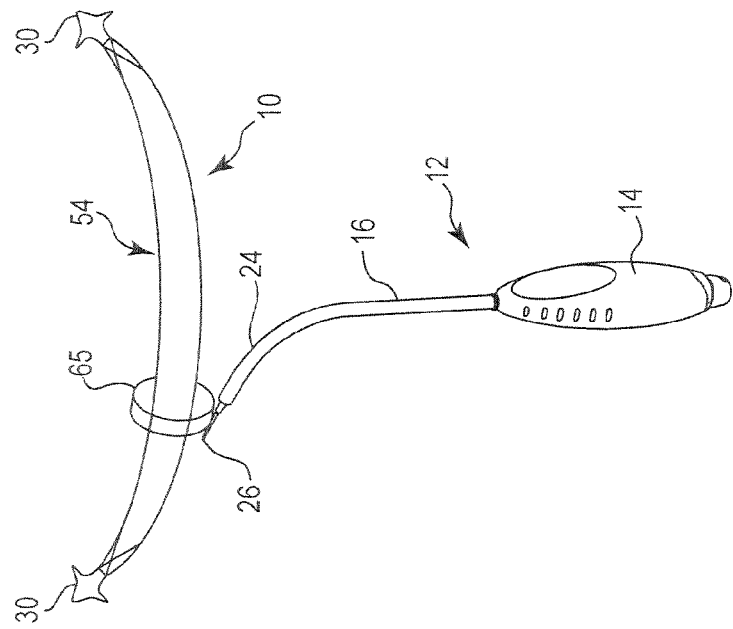
FIG. 18 shows a sling implant system having a sling implant, sliding yoke, and needle delivery device in accordance with embodiments of the present invention.

As shown in FIG. 18, the implant system 10 can include a yoke 65 adapted to slide or move along a length of the implant 54 or sheath 60. Again, the implant 54 can be constructed of mesh, solid material, hollow polymer, and the like. The needle device 12 is adapted to engage the yoke 65 to facilitate attachment with the implant 54 and guidance along the implant 54 and needle 16 during insertion and deployment.

A distal tip 26 of the needle 16 for various embodiments can be elongated to a level that promotes extending out from the lumen in the anchor 30, for holding or securing sutures, and the like. Sutures can be used for docking and alignment of the mesh ends 56 of the implant 54, and can be constructed of a relatively stiff material (e.g., wire, coated suture, semi-rigid polymer, etc.). Parts of the suture may need to remain flexible, portions of the suture can be flexible, while others are rigid or semi-rigid.

Further, the anchors 30 of the implant system 10 can include threading (e.g., female) adapted for twisting/rotating engagement with corresponding threads (e.g., male) in the distal tip 26 of the needle device 12. An actuator, rod, or similar mechanism, in the device 12 can facilitate selective threadable engagement and disengagement of the needle tip 26 with the anchors 30.

The needle device of FIG. 19 can include a distal portion having a bulbous or generally mushroom-shaped element 70 to selectively retain the anchor 30 on the needle tip 26. As such, an actuator 29 in the handle 14 can be activated or engaged to retract or withdraw the element 70 into the needle 16 lumen to release the anchor 30 from the needle tip during deployment. The element 70 can be generally deformable to permit retraction into and extension from the anchor 30 or other device.

As detailed herein, the anchors 30 can include pivotable or otherwise collapsible tines 31. The tines 31 can be in communication with the inner lumen 30a of the anchor 30, such that when the needle tip 26 is inserted into the lumen, the tines 31 pivot or collapse to facilitate insertion of the implant 54. At the point of deployment, the needle and tip 26 is removed, thereby causing the tines 31 to return or spring back to their extended position to facilitate fixation and tissue engagement. Pin, rod, or other flexibility or pivot features can be provided with the anchor tines 31 and anchor 30 in general to facilitate the described and depicted collapsibility and expandability.

The implant systems 10, their various components, structures, features, materials and methods may have a number of suitable configurations as shown and described in the previously-incorporated references. Various methods and tools for introducing, deploying, anchoring and manipulating implants to treat incontinence and prolapse as disclosed in the previously-incorporated references are envisioned for use with the present invention as well. Further, the system and its components or structures can be constructed of known and compatible materials know to those skilled in the art, including metals, polymers, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. A system for treating a pelvic condition, comprising:
   an implant having a support portion and one or more anchors;
   a needle delivery device having a handle body and a needle, wherein the needle includes a distal end portion adapted for selective engagement with the one or more anchors of the implant;
   a sheath having a proximal end and a distal end, and adapted to at least partially shroud a length of the needle; and
   an actuator in operable communication with the sheath, with the actuator including a barrel portion moveable in and out of the handle body such that activation of the actuator operably rotates the sheath about the needle such that the sheath does not move distally, to deploy the one or more anchors from the distal end portion.

2. The system of claim 1, wherein the one or more anchors include an end anchor on each end of the implant.

3. The system of claim 1, wherein the one or more anchors include extending anchor tines.

4. The system of claim 3, wherein the sheath includes a barb guard adapted to abut against the extending anchor tines.

5. The system of claim 1, wherein the sheath includes an angled end surface adapted to engage with the one or more anchors such that rotation of the sheath forces the one or more anchors from the distal end portion of the needle.

6. The system of claim 1, wherein the actuator is a pushable button in operable communication with the rotatable sheath.

7. The system of claim 1, wherein the needle is curved.

8. The system of claim 1, wherein the needle is straight.

9. The system of claim 1, wherein the one or more anchors include at least one internal lumen protrusion and the distal end portion of the needle includes a corresponding mating feature to facilitate snap engagement of the one or more anchors with the distal end portion.

10. The system of claim 9, wherein the at least one internal lumen protrusion includes two opposing internal lumen protrusions.

11. A system for treating a pelvic condition, comprising:
    a sling implant having a support portion and a tissue anchor;
    a needle delivery device having a handle housing and a needle, wherein the needle includes a distal tip adapted for selective engagement with the tissue anchor;
    a sheath having a proximal end rotatable within the handle housing, and a distal tip, with the sheath adapted to at least partially shroud a length of the needle; and
    an actuation mechanism in operable communication with the sheath and including a barrel element movable in and out of the handle housing, such that activation of the actuation mechanism operably rotates the sheath about the needle without moving the sheath distally to facilitate deployment of the tissue anchor.

12. The system of claim 11, wherein the tissue anchor includes extending anchor tines.

13. The system of claim 12, wherein the sheath includes a barb guard adapted to abut against the extending anchor tines.

14. The system of claim 11, wherein the sheath includes an angled end surface adapted to engage with the tissue anchor such that rotation of the sheath forces the tissue anchor from the distal tip of the needle.

15. The system of claim 11, wherein the actuation mechanism includes a pushable button in operable communication with the rotatable sheath.

16. The system of claim 11, wherein the needle is curved.

17. The system of claim 11, wherein the needle is straight.

18. The system of claim 11, wherein the tissue anchor includes at least one internal lumen protrusion and the distal tip of the needle includes a corresponding mating feature to facilitate snap engagement of the tissue anchor with the distal tip.

19. The system of claim 11, further including a second needle delivery device adapted to engage with a second tissue anchor of the sling implant.

20. The system of claim 11, wherein the actuation mechanism further includes a cam mechanism adapted to operably facilitate the rotation of the rotatable sheath about the needle.

21. A method for treating a pelvic condition, comprising:
providing an implant having a support portion and at least one anchor, a needle delivery device having a handle body and a needle having a distal end portion engaged with the at least one anchor, a sheath having a proximal end and a distal end, and configured to at least partially shroud a length of the needle, and an actuator in operable communication with the sheath, with the actuator including a barrel portion moveable in and out of the handle body; and
deploying the at least one anchor from the distal end portion by activating the actuator and rotating the sheath about the needle such that the sheath does not move distally.

* * * * *